United States Patent [19]

Tenenbaum

[11] Patent Number: 4,882,204
[45] Date of Patent: Nov. 21, 1989

[54] DIAPER SPRAY

[76] Inventor: Harvey Tenenbaum, 305 Woodland Acres, Maple, Ontario, Canada

[21] Appl. No.: 195,668

[22] Filed: Jul. 1, 1988

[30] Foreign Application Priority Data

May 5, 1988 [CA] Canada .................................. 566056

[51] Int. Cl.⁴ .............................................. B05D 1/12
[52] U.S. Cl. .................................... 427/180; 118/308; 604/367; 427/421
[58] Field of Search ................ 427/180, 421; 604/367, 604/369, 375, 378; 118/308

[56] References Cited

U.S. PATENT DOCUMENTS 4,055,184 10/1977 Karami .................................. 604/369
4,392,908 7/1983 Dehnel ................................ 427/180
4,486,468 12/1984 Gray ..................................... 427/180
4,623,560 11/1986 Ayers ................................... 427/180

Primary Examiner—Shrive Beck
Attorney, Agent, or Firm—Rogers, Bereskin & Parr

[57] ABSTRACT

The absorbency of a disposable diaper is increased by spraying the diaper with an aerosol spray containing absorbent powder, e.g. talcum, cornstarch or both. The powder particles are so fine (20–40 micron diameter) that the spray force drives many of them into the sub-surface layers of the diaper, thus increasing the absorbency of the diaper. At the same time, some powder remains on the diaper surface to help protect the skin of the wearer in the absence of urine.

6 Claims, 1 Drawing Sheet

DIAPER SPRAY

FIELD OF INVENTION

This invention relates to a device for spraying baby powder onto and into porous diapers, and to a method of increasing the absorbency of porous diapers.

BACKGROUND OF INVENTION

Disposable diapers are commonly used in industrialized societies, both for infants and for adults suffering from urinary incontinence. The primary function of such diapers is to absorb urine and any liquid accompanying fecal discharge so as to keep the wearer dry and to minimize skin contact with irritants in liquid excrements. Accordingly, manufacturers are constantly attempting to increase the absorbency of their diapers and to reduce the wetness at the skin-facing layer (i.e. the inner layer) of the diaper. Such diapers are therefore usually made relatively thick and porous.

Traditionally baby powder has been used to dust the person wearing the diaper, to absorb liquid excrements and to help keep the skin dry and protected. However this technique, while it provides some relief, has had only limited value because the baby powder becomes saturated with liquid excrements and then stays in contact with the skin for variable but commonly substantial periods of time.

SUMMARY OF THE INVENTION

The present invention offers a method of increasing the absorbency of diapers by impregnating the surface, and more importantly the subsurface layers, of the diaper, with an absorbent fine powder. In one of its aspects the invention provides a method of increasing the absorbency of a diaper, said diaper being of the kind having an inner porous skin-facing layer, a water resistant outer layer, and an absorbent layer therebetween, said method comprising:

(a) selecting a finely divided absorbent powder,
(b) spraying said powder onto said diaper
(c) the speed imparted to said powder during said step (b) being sufficiently high that a portion of said powder penetrates said skin-facing layer of said diaper and lodges within said absorbent layer of said diaper.

In another aspects the invention provides an aerosol diaper spray comprising:

(a) an aerosol container having a dispensing valve,
(b) a diaper spray material within said container, said diaper spray material comprising a finely divided absorbent powder,
(c) and a rapidly evaporating aerosol fluid within said container for spraying said material onto a porous diaper such as a disposable diaper, said fluid having a pressure sufficient to propel said powder in said material with a speed that will permit some of said powder to penetrate the porous skin-facing surface of said diaper and to lodge within the subsurface absorbent layer of said diaper.

Further objects and advantages of the invention will appear from the following description, taken together with the accompanying drawings in which.

DESCRIPTION OF PREFERRED EMBODIMENT OF INVENTION

Figure 1:
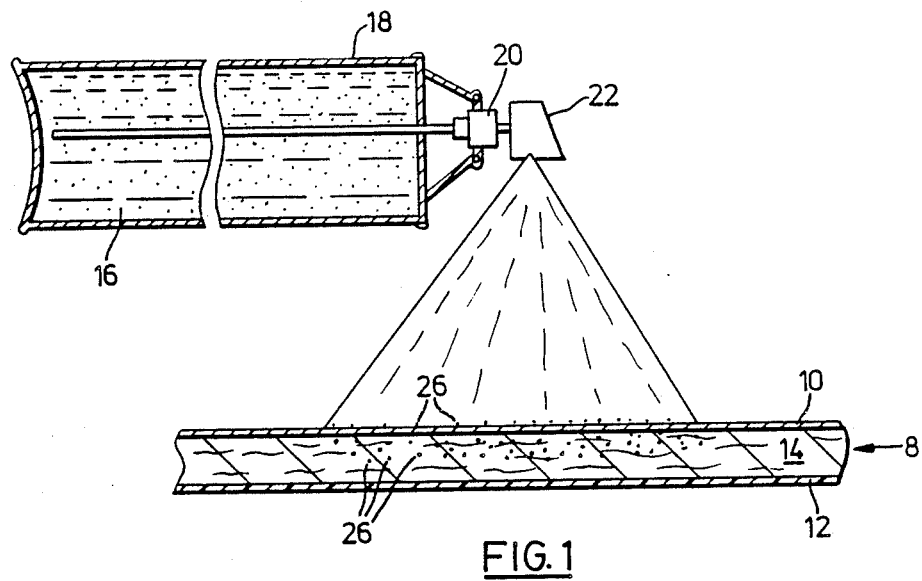
FIG. 1 is a diagrammatic view of an aerosol spray container according to the invention being used to impregnate a disposable diaper with powder.
Figure 2:
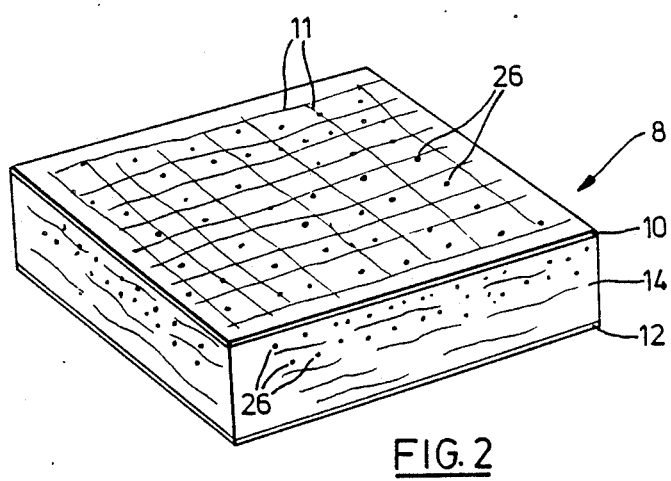
FIG. 2 is a perspective cut-away view of a portion of a disposable diaper showing the same impregnated with baby powder.

FIGS. 1 and 2 illustrate portions of a typical disposable diaper 8. Such diapers normally have an inner or skin-facing layer 10, an outer water resistant or waterproof plastic layer 12, and one or more thick layers of fibrous absorbent material 14 between the layers 10 and 12. The skin-facing layer 10 may be of paper or a natural or synthetic fabric and may be woven or nonwoven, but layer 10 is always of very open construction (usually one can "see" through it to some extent) in order to permit liquid to penetrate readily through it to the fibrous layers 14 below it. The open construction of layer 10 is indicated diagrammatically by lines 11 in FIG. 2.

The fibrous layers 14 are also usually of an open porous construction so that they will readily absorb and draw liquid into them, and yet so that they will provide softness and ease of accommodation to the wearer's shape.

According to the invention an absorbent powder mixture 16 is provided within an aerosol container 18. Container 18 is a conventional aerosol container containing a standard spray valve 20, nozzle 22, and inlet tube 24 which extends from the valve 20 into the container 18.

The absorbent powder used in the mixture 16 may be talcum, cornstarch, amorphous silica or precipitated chalk. A mixture of one or more of these powders is dispersed in the aerosol mixture 16, which may also contain alcohol, water, various perfumes, water soluble lanolin derivatives, and a propellent. The propellent may be FREON (trade mark), or it may be a non-fluoro carbon propellent such as carbon dioxide, nitrogen, or methylene chloride. Normally the propellent in the container is in liquid form wit the baby powder mixture dispersed therein. The propellent of course evaporates very rapidly when it is sprayed.

The aerosol nozzle 20 should be one which can produce a fine mist or spray in which the droplet size is 50 to 200 microns in diameter, and preferably 50 to 100 microns in diameter. The powder itself should be very fine in order to penetrate the diaper layers (as will be discussed), and therefore the size of the powder particles is preferably between 20 and 40 microns in diameter (one micron = $10^{-6}$ meters) The powder particles are contained in the aerosol droplets when the user sprays from the container.

In use, and as shown in FIG. 1, the aerosol container is brought to within a relatively close distance from the skin-facing layer 10 of the diaper (e.g. about 4 to 6 inches, preferably 6 inches), and then the mixture 16 within the aerosol container 18 is sprayed onto the diaper. The pressure in the aerosol container 18 is typically between 30 and 45 PSIG. With the method described, the powder mixture not only is sprayed onto the surface of the diaper but in addition penetrates into the subsurface layers of the diaper. Typically the depth of penetration is between 1 and 4 mm. The actual depth of penetration depends on how closely the aerosol container is held to the diaper, and on the pressure remaining in the aerosol container, and on the porosity of the diaper sample in question. The particles of powder on and in the diaper 8 are indicated in the drawings by dots 24.

Tests have found that surprisingly, the powder 24 sprayed onto and into the diaper substantially increases the absorbency of the diaper. Specifically the following test was conducted.

Ninety-six diapers of three brands (32 diapers of each of brands A, B and C) had the center 4 inch diameter circular section cut out of each diaper. A second set of 96 diapers of the same three brands (32 of each of brands A, B and C) also had the same center 4 inch diameter section cut out of each diaper. The 4 inch sections removed from the first set of 96 diapers will be referred to as sections A1, B1 and C1, while the sections cut from the second set of 96 diapers will be referred to as sections A2, B2, and C2.

Sections A1, B1 and C1 were all sprayed for two seconds with the powder diaper spray mixture 16, from a uniform distance of six inches. Each sprayed section was then weighed on an analytic balance. Each unsprayed section was also weighed on the same analytic balance.

While the diaper sections were being removed and sprayed, a urine-like solution (prepared as described below) was prepared. A uniform film of such solution was rolled with a clean fleece roller onto a shaved thigh.

The sprayed sections A1, B1 and C1, and the control sections A2, B2 and C2, were each secured in place by an elastic band on the shaved thigh for five minutes, and were then removed and weighed. The positions on the thigh were reversed for each alternate set of weighings. Any gain in weight was attributed entirely to the urine-like solution absorbed, and the percent difference in weight gain indicates superior absorbency caused by the diaper spray preparation. The results are shown in Table 1 below:

It is noted in Table 1 below, the control entries (samples 4, 8, 11 etc.) were tests in which no diaper spray preparation was used. Ideally the percent weight increase (or decrease) in the control samples should have been zero. The values shown indicate variability in the test samples used but were in fact all very close to zero.

TABLE 1

% INCREASE IN WEIGHT GAIN BY SPRAYED SECTION (A1, B1, C1) OVER UNSPRAYED SECTION (A2, B2, C2)

| Sample # | Samples Sprayed | % Increase in Weight Gain |
|---|---|---|
| 1 | A1 A2 | +17.2 |
| 2 | A1 A2 | +16.8 |
| 3 | A1 A2 | +21.1 |
| 4 | Control A1 A1 | −.2 |
| 5 | A1 A2 | +17.7 |
| 6 | A1 A2 | +17.6 |
| 7 | A1 A2 | +19.1 |
| 8 | Control A2 A2 | +.28 |
| 9 | A1 A2 | +16.3 |
| 10 | A1 A2 | +19.8 |
| 11 | Control A1 A1 | +.1 |
| 12 | A1 A2 | +17.8 |
| 13 | A1 A2 | +23.1 |
| 14 | Control A2 A2 | −.3 |
| 15 | A1 A2 | +16.8 |
| 16 | A1 A2 | +17.9 |
| 1 | B1 B2 | +21.7 |
| 2 | B1 B2 | +20.6 |
| 3 | B1 B2 | +20.3 |
| 4 | Control B1 B1 | +.3 |
| 5 | B1 B2 | +19.9 |
| 6 | B1 B2 | +20.6 |
| 7 | B1 B2 | +20.4 |
| 8 | Control B2 B2 | +.1 |
| 9 | B1 B2 | +21.7 |
| 10 | B1 B2 | +22.3 |
| 11 | Control B1 B1 | +.1 |
| 12 | B1 B2 | +22.5 |
| 13 | B1 B2 | +21.6 |
| 14 | Control B2 B2 | +.2 |
| 15 | B1 B2 | +21.9 |
| 16 | B1 B2 | +20.8 |
| 1 | C1 C2 | +19.8 |
| 2 | C1 C2 | +19.3 |
| 3 | C1 C2 | +18.8 |
| 4 | Control C1 C1 | −.2 |
| 5 | C1 C2 | +21.1 |
| 6 | C1 C2 | +19.7 |
| 7 | C1 C2 | +18.8 |
| 8 | Control C2 C2 | — |
| 9 | C1 C2 | +21.1 |
| 10 | C1 C2 | +18.8 |
| 11 | Control C1 C1 | +.1 |
| 12 | C1 C2 | +18.7 |
| 13 | C1 C2 | +19.3 |
| 14 | Control C2 C2 | −.3 |
| 15 | C1 C2 | +24.1 |
| 16 | C1 C2 | +20.8 |

The urine-like solution was prepared as set forth in Table 2 below:

TABLE 2

| Ingredient | Weight in Grams |
|---|---|
| Water | 140 |
| Urea | 3 |
| Uric acid | .04 |
| Amino acids | .21 |
| Phosphates | .11 |
| Ammonia | .07 |

The urine-like solution was warmed to 37° C. before being applied to the shaved thigh.

A typical spray powder mixture 16 is prepared using ingredients selected from the following list, set forth in Table 3 below:

TABLE 3

| Ingredient | Percent by Weight |
|---|---|
| Talcum powder (acts as absorbent powder) | 5–15 |
| Cornstarch (acts as absorbent) | 0–4.3 |
| Magnesium stearate (an optional absorbent which gives enhanced absorption) | 1.5–3.6 |
| Isopropyl myristate (an optional stabilizing agent to maintain uniform dispersion of the powder in the liquid propellant) | 2.7–4.5 |
| Amorphous silica (an absorbent and also a lubricant to provide a smooth feel between the diaper surface and the skin) | 0–1.8 |
| Precipitate chalk (an absorbent material) | 0–1.6 |
| Lanolin extract (a skin protectant) | .1–1.6 |
| Alocel-C (trade mark) (derivative of aloe vera extract, acting as a skin protectant) | .3–4.5 |
| Methyl paraben (a preservative to prevent bacterial growth) | .2–.4 |
| Freon (trade mark) (a propellant) | 10–85 |
| Hydrocarbon propellant (alternative to | 10–50 |

TABLE 3-continued

| Ingredient | Percent by Weight |
| --- | --- |
| Freon) | |

It will be seen from Table 1 that spraying the diaper material with the diaper spray of absorbent particles according to the invention increased the absorbency of the diaper by an average of about 18.7%. The significant increase in absorbency which is achieved means an increase in dryness and therefore comfort for that person diapered, and also results in a lower likelihood of chaffing or diaper rash occurring. At the same time, some powder remains on the diaper surface to help protect the skin directly (in the absence of urine).

The weight of diaper spray mixture applied to each diaper section during the test was about 200 mg. Since the A2, B2, C2 samples normally absorbed about 4 grams of liquid each, the average increase in weight of liquid absorbed by each sample was about 0.75 grams, which was much more than 200 mg of powder could itself absorb. The increase in weight of liquid absorbed was because the powder was forced by the pressure of the aerosol into the subsurface layers of the diaper and helped to draw liquid into those layers, thereby increasing the absorbency of the diaper in the subsurface layers.

It will be appreciated that the particular formulation of the diaper spray can be changed, so long as a very fine absorbent powder is used which can be forced by the pressure of the aerosol into the subsurface layers of the diaper. However preferably a stabilizing agent is used so that the powder will remain suspended (so that the container need not be shaken), and preferably a skin protectant and a lubricant are also used.

A further advantage of the invention as described is that the powder need not be applied to the person being diapered. In addition, since much of the powder is driven by the force of the aerosol into the diaper itself, there is less powder on the surface of the diaper to fall off the diaper when the diaper is being moved.

I claim:

1. A method of increasing the absorbency of a diaper, said diaper being of the kind having an inner porous skin-facing layer, a water resistant outer layer, and an absorbent layer therebetween, said method comprising:
    (a) selecting a finely divided absorbent powder,
    (b) spraying said powder onto said diaper,
    (c) the speed imparted to said powder during said step (b) being sufficiently high that a portion of said powder penetrates said skin-facing layer of said diaper and lodges within said absorbent layer of said diaper.

2. A method according to claim 1 wherein said absorbent powder comprises particles of between 20 and 40 microns in diameter.

3. A method according to claim 1 wherein said powder is sprayed from an aerosol container which is pressurized to a pressure of at least between 30 and 45 PSIG with a rapidly evaporating aerosol fluid.

4. A method according to claim 1 wherein said powder includes, mixed therein, a minor proportion of a skin protectant material.

5. A method according to claim 1 wherein said powder is selected from one or both of the materials talcum and cornstarch, and wherein said powder has, mixed therewith, a minor ingredient of a skin protectant material and a minor ingredient of a bacteria growth inhibiting material.

6. A method according to claim 1 wherein said diaper is a disposable diaper.

* * * * *

UNITED STATES PATENT AND TRADEMARK OFFICE
CERTIFICATE OF CORRECTION

PATENT NO. : 4,882,204

DATED : November 21, 1989

INVENTOR(S) : Tenenbaum

It is certified that error appears in the above-identified patent and that said Letters Patent is hereby corrected as shown below:

On the title page, item [21]   Appl. No.: 195,668 should read -- [21]  Appl. No.: 195,568  --.

Signed and Sealed this

Eleventh Day of December, 1990

*Attest:*

HARRY F. MANBECK, JR.

*Attesting Officer*     *Commissioner of Patents and Trademarks*